United States Patent [19]

LeVeen et al.

[11] 4,381,380
[45] Apr. 26, 1983

[54] THERMOPLASTIC POLYURETHANE ARTICLE TREATED WITH IODINE FOR ANTIBACTERIAL USE

[76] Inventors: Harry H. LeVeen; Jeanette L. Rubricius, both of 321 Confederate Cir., Charleston, S.C. 29407; Eric G. LeVeen, 3-3 Woodlake Rd., Albany, N.Y. 12203; Robert F. LeVeen, 312 Lombard St., Philadelphia, Pa. 19147

[21] Appl. No.: 203,432

[22] Filed: Nov. 3, 1980

[51] Int. Cl.³ .................... C08G 18/83; A61M 25/00; A61K 31/74; C08G 71/02
[52] U.S. Cl. .................................. 525/452; 128/260; 264/310; 424/78; 521/53; 521/163; 521/905; 525/453; 525/440; 528/44; 604/265
[58] Field of Search .................... 521/163, 53, 905; 525/1, 452, 453, 440; 128/260, 349; 264/310; 424/78; 528/44

[56] References Cited

U.S. PATENT DOCUMENTS

| | | | |
|---|---|---|---|
| 3,235,446 | 2/1966 | Shelanski et al. | 521/174 |
| 3,401,005 | 9/1968 | Katz | 428/907 |
| 3,566,874 | 3/1971 | Shepherd | 424/14 |
| 3,598,127 | 8/1971 | Wepsic | 424/21 |
| 3,694,413 | 9/1972 | Batzer et al. | 525/440 |
| 3,898,326 | 8/1975 | Cantor et al. | 424/80 |
| 3,987,797 | 10/1976 | Stephenson | 424/26 |
| 4,010,259 | 3/1977 | Johansson | 424/78 |
| 4,017,407 | 4/1977 | Cantor et al. | 424/80 |
| 4,054,139 | 10/1977 | Crossley | 128/260 |
| 4,094,967 | 6/1978 | Gilbert | 424/28 |
| 4,113,851 | 9/1978 | LeVeen et al. | 424/28 |
| 4,239,727 | 12/1980 | Myers et al. | 264/321 |

FOREIGN PATENT DOCUMENTS 824215 11/1959 United Kingdom .................... 525/1

OTHER PUBLICATIONS

Whittington's Dictionary of Plastics, 1st Ed., Technomic, Stamford, Conn., (1968), pp. 238-239.

*Primary Examiner*—H. S. Cockeram
*Attorney, Agent, or Firm*—Gipple & Hale

[57] ABSTRACT

There is provided a polymeric bacteriocidal composition comprising a thermoplastic, partially cross-linked polyurethane having —NH—(C═O)—O— urethane linkages and/or urea linkages —NH—(C═O)—NH— and iodine complexed with a sufficient number of these linkages to provide bacteriocidal properties to said composition. The polyurethane has an average molecular weight between 35,000 and 50,000, an ultimate elongation of 200 to 800% and a Shore A scale hardness of 60 to 95. The composition is shaped into a conventional medical appliance form, e.g. a catheter.

18 Claims, No Drawings

THERMOPLASTIC POLYURETHANE ARTICLE TREATED WITH IODINE FOR ANTIBACTERIAL USE

The present invention relates to polymeric bacteriocidal compositions comprising a thermoplastic polyurethane which is complexed with iodine, for use in antibacterial applications, and more particularly to such compositions which are used in connection with medical appliances.

BACKGROUND OF THE INVENTION

The incidence of bacterial infection caused by bacterial contamination of medical appliances has never been reduced to a satisfactory level. This is particularly true in connection with medical appliances which cannot normally be sterilized in autoclaves or which when in use encounter bacteria containing environments. For example, sutures, catheters, surgical tape, tubings, sponges, gloves, pads, surgical covers and certain medical instruments cannot be autoclaved to insure sterility but often must be used in areas where pathogenic bacteria are encountered. Accordingly, for such medical appliances, the art has long sought means and methods of rendering those medical appliances antibacterial and, hopefully, self-sterilizing. The general approach in the art has been that of coating the medical appliance, or a surface thereof, with a bacteriocide. However, since most bacteriocides are partly water soluble, or at least require sufficient solubilization for effective antibacterial action, simple coatings of the bacteriocides have been proven unreliable. For this reason, the art has further sought to incorporate the bacteriocides into the medical appliance or at least provide a stabilized coating thereon.

The art has taken many different directions in attempting to solve this problem, but finding the combination of effective bacteriocides and means of retaining that bacteriocide in or on the medical appliance has either eluded the art in regard to some applications, or the art has not found totally satisfactory solutions in regard to other applications. For example, many of the medical appliances which encounter the above noted problem are made of non-metallic materials, such as plastics, cat gut, and gelatin. Since these materials cannot be adequately autoclaved, at least in connection with the environment of use, these types of medical appliances present the problem in its most difficult form and the problem has never been solved. One of the earlier attempts to solve this problem is discussed in U.S. Pat. No. 1,006,854, wherein cat gut, for suture purposes, is treated with iodine to disinfect the suture material. However, since the iodine is not tightly bound to the cat gut it is rapidly released during use and quickly inactivated.

With the increased use of polymeric materials for construction of medical appliances, such as catheters, artificial blood vessels, injection tubing, surgical tape and the like, the problem of a self sterilizing polymer has become more important. The art, therefore, sought combinations of plastics and antibacterial agents wherein the antibacterial agent could be fixedly attached to or incorporated in the plastic so that the combination thereof could be used for the manufacture of these plastic medical appliances. This relatively recent effort in the art has taken a myriad of different approaches. For example, U.S. Pat. No. 3,401,005, discloses that a combination of polyvinylpyrrolidone and iodine could be applied to cotton gauze and the like and when dried would have a germicidal characteristic. In a similar effort, a combination of polyvinylpyrrolidone and iodine was placed in absorbable, gelatin foams to produce surgical sponges. It was also found that iodine could actually be complexed with polyvinylpyrrolidone and the complexed composition would slowly release iodine under use conditions. Solid polyvinylpyrrolidone complexed with iodine is disclosed in U.S. Pat. No. 3,898,326 as useful as a disinfectant material and U.S. Pat. No. 4,017,407 extends that composition to include other ingredients such as detergents.

Improved polyvinylpyrrolidone/iodine complexes are disclosed in U.S. Pat. No. 4,094,967, for coating dressing materials and the like, but the art has not been successful in using polyvinylpyrrolidone/iodine complex as a material of construction for producing medical appliances. U.S. Pat. No. 4,113,851, suggests complexing iodine with a preformed polymer of 2-pyrrolidone and then treating with an emulsion of a polyacrylic acid to impregnate the polyvinylpyrrolidone/iodine complex with the acid.

The lack of success of producing medical appliances with complexed polyvinylpyrrolidone and iodine led the art toward other approaches and U.S. Pat. No. 4,010,259 suggests complexing iodine with polysaccharide, such as starch, dextran or cellulose, but here again, these materials are not suitable for materials of construction of most medical appliances.

In yet another approach, U.S. Pat. No. 3,598,127 suggests infusing an antibacterial substance, such as neomycin and the like, into a polysiloxane rubber, while U.S. Pat. No. 4,186,745 suggests a similar approach with microporous polyethylene, polypropylene, or polyflurocarbon polymers. These approaches are merely mixtures and the bacteriocidal agent is not chemically combined to the plastic and slowly released.

In an approach somewhat similar to the above, antibiotics and germicides, e.g. penicillin and cetylpyridinium chloride, are infused into a hydrophilic polymer for coating medical appliances such as catheters, according to the disclosure of U.S. Pat. No. 3,566,874. Such antibiotic approaches have other limitations in that the antibiotic is not effective against all organisms.

In another approach, multifilament suture strands are impregnated with a water soluble antimicrobial agent, such as penicillin, and then coated with polyurethane polymer so as to maintain the antimicrobial agents. A similar approach is disclosed in U.S. Pat. No. 3,987,797, where a surgical suture is coated with a copolymer of polyquaternary polyurethane and a polyanionic polymer, such as heparin and then treated with an antimicrobial compound, such as penicillin. There have also been efforts to incorporate bacteriocides, in gross, in polymers simply by mixing with the polymer, and U.S. Pat. No. 2,947,282, is representative thereof.

Polyurethane would be most useful in producing medical appliances of the present nature, and efforts along the above lines have also been made to render those polyurethane appliances self-sterilizing. For example, U.S. Pat. No. 3,235,446, prepares a polyurethane foam by the reaction between a liquid polyfunctional hydroxyl terminated polyether or polyester and a liquid polyfunctional organic di-isocyanate, with subsequent exposure to water so that a foam results. The resulting plastic is a thermoset. The foam is then treated with an iodine solution. This approach is successful in producing a prefoamed polyurethane complexed with iodine, but materials prepared in this manner are not thereafter convertible into other medical appliances since they are not thermoplastic but thermosetting. Few or no medical devices are manufactured with thermosetting plastic resins. In addition, the diisocyanate used in the manufacture is a toxic substance and difficult to handle.

U.S. Pat. No. 3,897,797 relates specifically to thermosetting polyurethanes which are different from the thermoplastic polyurethanes which we have investigated. Shelenski, Mills and Levenson have chosen a special situation in thermosetting polyurethane resins by reacting isocyanetes with relatively high molecular weight (M.W. 1000) compounds having terminal hydroxal groups and containing not less than 30% ethylene oxide. Yet, short chain polyalcohols are often used in mixtures to provide for sparse cross-linking and these sparsely cross-linked compounds can be thermoplastic. Although such cross-linked thermoplastic resins have high tear resistance, steric hindrance renders the

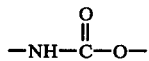

urethane linkages which complex with iodine inaccessible in highly cross-linked plastics. This factor may have discouraged the investigation of the possibility of complexing iodine onto thermoplastic polyurethanes which are only sparsely cross-linked.

As can thus be appreciated, considerable effort has been expended, yet success in the art has been elusive. This is particularly true in connection with the manufacture of medical appliances, such as catheters and the like which should not only be sterile, but have good tensile properties and yet be relatively inexpensively manufactured. In this latter regard, such medical appliances are normally shaped, e.g. by molding or extruding a thermoplastic material, which thermoplastic material, inherently, has the tensile properties required for the particular medical appliance. This means of manufacture is relatively inexpensive, as is required, and can be accurately controlled for size, shape, uniformity and reliability. Thus, any practical solution to the above problem must also include the ability for the medical appliance to be molded into the particular shape required by the medical appliance.

It would therefore be of substantial advantage to the art to provide a shapeable polymeric composition which is also bacteriocidal and which, in addition, has the required tensile properties for allowing formation thereof into practical and usual medical appliances of a relatively inexpensive nature.

OBJECTS OF THE INVENTION

It is therefore an object of the invention to provide a polymeric, bacteriocidal composition which is thermoplastic in nature and can be shaped into usual medical appliances in an inexpensive manner. It is a further object of the invention to provide such composition which is also bacteriocidal. It is a further object of the invention to provide a shaped form of that composition, particularly forms which are in the shape of usual medical appliances, such as sutures, catheters, tape, tubing, etc. It is another object of the invention to provide a method of producing such medical appliances. Other objects will be apparent from the following description and claims.

BRIEF DESCRIPTION OF THE INVENTION

The invention is based on three primary considerations. Firstly, as can be appreciated from the above, a number of different polymers have been used in the art for making medical appliances of the present nature. Each of these polymers has its own set of advantages and disadvantages. While polyurethane polymers have been known for making medical appliances, e.g. the foams of U.S. Pat. No. 3,235,446, discussed above, polyurethanes have not found wide acceptability for such appliances. As is known, polyurethanes may be made in an essentially uncross-linked or in an essentially cross-linked state. The uncross-linked polyurethanes have relatively weak tensile properties and while they may be made into relatively fragile films and the like, they are not acceptable for appliances which require more exacting physical properties. Polymers on the other hand, while the fully cross-linked polyurethanes have exceptionally good physical properties, they are not thermoplastic and cannot be transformed into molded or extruded structures. For example, the foams of U.S. Pat. No. 3,235,446, discussed above, are not thermoplastic in the nature required for accurate molding of medical appliances. Thus, the art has looked to other more conventional thermoplastic materials, as discussed above, for producing medical appliances of the present nature.

Thermoplastic compounds are chemically and structurally different from the thermosetting polyesters and polyethers mentioned in U.S. Pat. No. 3,987,797. Frequently they are sparsely cross-linked with polyamines rather than alcohols to yield urea type linkage

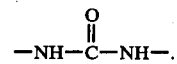

Our investigations reveal that this type of linkage complexes with free iodine to an even greater extent than does the urethane linkage. Because the different linkages have varying accessibility and varying degrees of chemical binding with the iodine the dissociation free iodine from bound iodine will vary considerably at water plastic interface depending on the extent of iodinization. If the polyurethane is treated with dilute iodine solutions, those groups with the greatest avidity for iodine will react first and will be the least dissociable into free iodine. By increasing concentrations of iodine used in treating the thermoplastic polyurethane, bonds which are easily broken will be complexed at higher concentrations. These bonds will yield their iodine more readily and will produce higher concentrations of free iodine at an aqueous interface with the plastic surface. It is the free iodine which is responsible for the bacteriocidal properties. Concentrations of iodine as low as 0.5 ppm have been shown to kill staphylococcus aureus and other pathogens in 50-60 seconds. (Am Jr. Public Health 60:535 1970; Soap Sanit Chem 28:149 1952). The ability to render extruded and injection molded products biocidal would make self-sterilizing medical products a practical reality since the majority of useful medical devices cannot be fabricated with thermosetting urethane plastics, but can be extruded or injection molded.

However, it has been discovered that a relatively narrow group of polyurethane polymers have a unique combination of properties in that they are sufficiently thermoplastic to be molded in conventional molding and extrusion apparatuses, while at the same time they present physical properties quite sufficient for the usual medical appliances. In addition, it has also now been found that these polymers are also capable of complexing with iodine and retaining that complexed iodine in an advantageously releaseable form. This relatively narrow group of polyurethane polymers is referred to in the art as sparingly (or partially) cross-linked polyurethanes. The cross-linking is sufficient that at room temperature or thereabouts, the polymers have quite acceptable physical properties, but at higher temperatures, e.g. at molding temperatures, the cross-linking is insufficient to prevent deformation and those polymers may, indeed, be molded. Polymers of this nature can be made by a variety of processes and with a number of different starting materials. However, these polymers will have an average molecular weight of between 35,000 and 50,000, an ultimate elongation of between 200 and 800% and a Shore A scale hardness of 60-95. Thus, the polymers useful in the present invention may be characterized by their physical properties, as aforenoted.

The second major consideration which resulted in the present invention is the discovery that even though these polyurethane materials are sparingly cross-linked, the degree of steric hindrance does not prevent the reactive groups from adequately complexing with iodine. There are sufficient linkages at the surface of the polymer that can complex with iodine and slowly release the iodine to create a bacteriocidal environment. Thus, the complexed iodine is slowly dissociable from the polyurethane in sufficient concentrations to create a germ free zone around the plastic and to kill the bacteria on contact. For example, when the iodine complexed polyurethane of the present invention is in a gaseous atmosphere, such as air, sublimation of the iodine is quite low and the iodine complexed polyurethane retains its bacteriocidal properties for prolonged periods of time. However, when in an aqueous environment, the dissociation of the iodine is increased and sufficient free iodine is liberated to render the surface concentration of iodine bacteriocidal and thus keep the surface of the plastic sterile. This liberation is not so rapid that the iodine is so quickly removed from the polyurethane as to injure or kill normal tissues. The polyurethane becomes a true iodophor.

The third major consideration, is that these polyurethane polymers may be preformed into the medical appliances desired, and the iodine can be successfully incorporated into those preformed shapes, even though the preformed shape is not open or porous in the nature of foam or the like, but closed and impervious, in the nature of a solid tube or the like. This renders it unnecessary to treat the plastic prior to extrusion or injection molding.

Thus, briefly stated, the present invention provides a polymeric bacteriocidal composition. That composition contains a thermoplastic, sparingly cross-linked polyurethane having —O—(CO)—NH— urethane linkages and iodine complexed with a sufficient number of said linkages to provide bacteriocidal properties to the composition. The polyurethane of the composition has an average molecular weight of between 35,000 and 50,000, an ultimate elongation of 200 to 800% and a Shore A scale hardness of 60-95.

That composition may be rendered into a shaped form by conventional thermoplastic molding techniques, e.g. compression molding, transfer molding, injection molding, extrusion, casting and the like, and more particularly, may be formed into medical or hospital appliances, such as sutures, catheters, tape, tubing, sponges, gloves, instruments and the like.

Within the constraints of the polyurethanes useful with the invention, as stated above, the polyurethane can range from a semi-rigid to a flexible composition, or may be foamed with the aid of a blowing agent or the like.

The shaped form may be prepared by shaping the composition into a preformed shape and contacting the preformed shape with a solution of iodine, e.g. a tincture and or aqueous solution of iodine.

DETAILED DESCRIPTION OF THE INVENTION

As noted above, polyurethane polymers can have an exceedingly wide range of properties. These properties can range from a very weak film, suitable only for paints and the like, to an essentially rigid structure, quite suitable for a building material, e.g. rigid urethane foams. In between these extremes, the polyurethane polymers may be relatively soft and have low ultimate elongations, e.g. 100% or less or may be quite tough, but not thermoformable. This range of properties induced in polyurethane polymers is a result, primarily, of the molecular weight of the polymer and the degree of cross-linking, or absence of cross-linking. Thus, there is almost an infinite variety of properties which can be achieved with polyurethane polymers.

According to the present invention, it was discovered that a relative narrow group of polyurethane polymers has the unique combination of properties which make it suitable for medical appliances, i.e. mechanically strong, relatively elastic, resistant to common solvents, and, more importantly, can be shaped and will complex an adequate amount of iodine in an advantageously releasable fashion. To achieve this unique set of properties, the polyurethane must have an average molecular weight of between 35,000 and 50,000 and it must be sparingly cross-linked.

In this latter regard, the term "sparingly cross-linked" has reference to the relative number of cross-linked bonds in the polyurethane polymer. For example, the polyurethane polymer may be prepared with relatively short chain polyalcohols and toluene diisocyanate which will give a relatively high density of potential cross-linking sites. However, when the cross-linking is controlled so that there are only a small number of cross-linked sites, the resultant polymer will be only sparingly cross-linked. Such a "sparingly cross-linked" polyurethane polymer has a sufficient number of NCO grouped on the surface to complex iodine. On the other hand, for example, with long chain compounds containing only a single terminal alcohol group, the degree of cross-linking is almost nil since cross-linking occurs by the reaction of an alcohol with a isocyanate group and at least two alcohol groups are required for cross-linking. The length of the chain for the number of alcohols will determine the degree of cross-linking. When all cross-linkable sites are cross-linked, but the total degree of cross-linking for any polymer is still low owing to the limited number of cross-linkable sites, the polymer is regarded as "sparingly cross-linked". Thus, it is not the particular composition of the polyurethane which is important in determining its thermoplastic properties, but the degree of cross-linking or cross-link density in the polyurethane polymer. This degree of cross-linking will determine the polymer's molecular size and though physical properties of the polyurethane are modified by its chemical composition, the tear resistance and many of the physical properties are determined by the degree of cross-linking in the polymer. Accordingly, some "sparingly cross-linked" polyurethane polymers have an ultimate elongation of 200 to 800%, a Shore A scale hardness of 60–95 and are thermoplastic. In this latter regard, the term "thermoplastic" means that the polymer is shapeable in conventional shaping machines, e.g. extruders and molders, at temperatures less than 400° F. On the other hand, it also means that the polymer is not meltable at temperatures less than 200° F.

While the foregoing describes sparingly cross-linked polyurethane polymers, it is preferred that the ultimate elongation be between 200 and 400% and the hardness be between 70 and 90. It is also preferred, for convenience of manufacture and source of materials, that the polyurethane polymer be a sparingly cross-linked form of a polyurethane made from a polyether or polyester, the technology and connection with which is well known to the art and will not be described herein for sake of conciseness.

The polyurethane polymer of the above nature has been found to readily accept iodine solutions for complexing the iodine with the urethane linkages. It has also been found that such complexed iodine is releasable from the polyurethane in advantageous amounts and rates. The release is neither too slow nor too fast for practical use in aqueous environments, but is of a rate that the surface of a shaped form will have an ample supply of released iodine for bacteriocidal purposes, but will not release the iodine at such a rate that the shaped form will rapidly be depleted of the iodine and injure normal tissue. In addition, it has been found that these polyurethane polymers retain the iodine in a non-aqueous atmosphere for prolonged periods, so that sublimation of the iodine, e.g. in an air atmosphere, is considerably reduced and the iodine will be retained in that atmosphere for long periods of time, e.g. during normal shelf storage and the like.

The duration of release of iodine is roughly proportional to the amount of iodine complexed with the polyurethane. Sufficient iodine is released to be in equilibrium with a free iodine content in the immediate environment of between 5 to 25 parts per million. As the iodine is bound in the tissues or carried away by the blood stream or lymphatic circulation, more is released. For example, if the complexing is carried out for an extended period of time, saturation of complexed iodine will take place. Equilibrium will be established with this pool. The amount of iodine at the surface is essentially a sterilizing amount of iodine. Saturation amounts can easily be determined by following the uptake of iodine during the complexing process, as described in detail below. On the other hand, small amounts of iodine can be complexed with the polyurethane, but in this case, self-sterilizing conditions of the surface will not normally be achieved, although improved bacteriocidal properties will be achieved. Minimum iodine complexing can also be controlled during processing thereof, as explained more in detail below, by following the uptake of iodine during the complexing step.

The polymeric composition may be molded into a shaped form in any manner desired, but primarily for purposes of the present invention that shaped form will be a medical or hospital appliance, although the shaped form may be configured as a packaging film or a package, particular for hospital supplies and the like. Typical medical appliances are sutures, catheters, surgical tape and tubing, sponges, surgical gloves, surgical pads, patient bed or instrument covers and instruments themselves, e.g. infusion tubes and the like. Alternately, the composition may be in the form of a coating. For example, the medical appliance may be a sanitary appliance, e.g. a bed pan, having a coating of the bacteriocidal composition thereon. While that coated composition will have the properties as described above, especially the moldable properties, that composition may be applied as a paint or lacquer via a solvent carrier. Molding and coating techniques for producing such appliances are well known in the art and need not be described herein for sake of conciseness.

Since it is only the surface of the medical appliance where bacterial contamination takes place, the iodine will normally be complexed into the preformed shape on or near at least a part of the surface of the preformed shape, consistent with placing sufficient iodine on or near the surface to provide bacteriocidal properties for an extended period of time. It is not necessary that the iodine be complexed throughout the preformed shape and the complexing is carried out with this purpose in mind.

In regard to the method of making the medical appliance, the polyurethane polymer is shaped into a preformed shape, of desired configuration. That preformed shape is then contacted with a solution of iodine. The temperature of the solution is not critical and can be from as low as near the freezing point thereof, to near the boiling point thereof, but room temperature or above is preferred, e.g. 20° C. to 60° C. The amount of iodine in the solution can also vary as desired, but concentrations of as little as 1% up to 15% are quite satisfactory. However, in practice, where the uptake of iodine is to be more carefully controlled, concentrations of about 2 to 4%, e.g. 3% of iodine are preferred, since lower concentrations still provide a relatively rapid uptake of iodine, but at a predictable and controllable rate. The iodine may be advantageously an aqueous solution, a tincture or a combination thereof, e.g. a 50% alcoholic solvent and, if desired, containing 1% potassium iodide. Indeed, the iodine solutions disclosed in the U.S. patents, noted above, dealing with polyvinylpyrrolidone are quite acceptable for the present invention and further details will not be given herein for the sake of conciseness.

The amount of iodine uptake will be dependent upon the concentration of the iodine in the solution, the solvent of the iodine solution, the temperature of the solution, and the time of contact with the iodine solution. However, generally speaking, the period of contact will be for at least 5 minutes and more usually at least an hour. While the contact time can be up to 48 hours or more, the uptake of iodine after about 10 to 12 hours markedly decreases, and these extended times do not produce substantially greater amounts of complexed iodine in the polyurethane polymer.

More importantly than either the particular contact time, concentration, or temperature of the solution, is the ultimate uptake of iodine by the preformed shape. This can be measured directly by conventional methods for determining the iodine content of the polymer or it may be measured indirectly by analyzing the decrease of iodine concentration in the contacting solution. Irrespective of the method of measurement, a graph of iodine uptake versus contact time for any iodine solution, at a given temperature, can be established and can be used for very accurately controlling the iodine uptake.

The iodine solution may contact the preformed shape by immersing the preformed shape into the solution, or the solution may be sprayed or otherwise dispersed thereon. It is only necessary that the solution be in intimate contact and uniformly dispersed about the preformed shape. For convenience, the preformed shape is simply immersed in the iodine solution, although for larger objects, spraying of the iodine solution may be utilized.

After the required contact with the iodine solution, the preformed shape will normally be washed to remove excess iodine solution from the surface thereof. While any wash may be used, in this regard, the liberal use of water for 48 hours has proven adequate to remove all free uncomplexed iodine.

As an alternative process, to the process described above, the contacting with the iodine solution may be under elevated pressures. In certain medical appliances, it is necessary to have a porous or microporous structure. In these cases it may be difficult to contact all of the porous or microporous interstices with the iodine solution, particularly with smaller pores in the porous material and higher surface tensions of the iodine solutions. In these special cases, the preformed shape in the iodine solution may be subjected to elevated pressures, e.g. 1 to 50 atmospheres in order to force the iodine solution into the porous structure. After such treatment, while not necessary, a similar elevated pressure wash may be utilized, with or without a vacuum withdrawing of iodine and wash solution.

The invention will now be illustrated by the following examples, although it is to be understood that the invention is not restricted thereto, but extends to the breadth of the foregoing specification and the following claims. In the examples, as well as in the specification and claims, all percentages and parts are by weight unless otherwise specified.

EXAMPLE 1

Sparingly cross-linked polyurethane polymer (Estane-58271, manufactured by B. F. Goodrich Co.) was tested and found to have an elongation of approximately 400% and a Shore A scale hardness of 86. The polymer was compounded with a blowing agent (sodium bicarbonate) and heated to a flowable state, i.e. a temperature of approximately 350° F., whereby the polymer was foamed. The gross foam was cut into sections of approximately ½" in diameter and 1/8" thick. Solutions of iodine in a 50% aqueous/alcohol solvent were prepared. The iodine concentration in the solutions were 0.125%, 0.25%, 0.5%, 1% and 2%. The cut sections were immersed in the iodine solutions for a period of 5 minutes. Thus, the uptake of iodine in each of the different solution concentrations would be essentially proportional to the concentration of iodine in the solutions. After removal from the iodine solutions, the cut sections were washed with alcoholic potassium iodide.

Agar plates, containing Hank's solution, were prepared and into these agar plates were placed the cut sections of the foam which had been complexed with iodine in the different iodine concentration contacting solutions. One plate was inoculated with *S. aureus* and another plate was inoculated with *Proteus vulgaris*. The plates contained a dye for revealing the absence of bacterial growth.

After 48 hours of incubation at 30° C., the plates were examined for bacterial growth. The determination was that of measuring the diameter of absence of bacterial growth around each circular cut section and comparing that diameter, as a ratio, with the diameter of the cut section. Thus, where no bacterial growth inhibition takes place, the ratio is 1:1. The results were as follows:

| % I Solution | Diameters Ratio | Organism |
|---|---|---|
| 0.125 | 1:1 | *S. aureus* |
| 0.25 | 1.05:1 | " |
| 0.50 | 1.1:1 | " |
| 1.0 | 1.5:1 | " |
| 2.0 | 2.5:1 | " |
| 0.125 | 1:1 | *Proteus vulgaris* |
| 0.25 | 1.05:1 | " |
| 0.50 | 1.15:1 | " |
| 1.0 | 1.5:1 | " |
| 2.0 | 2.6:1 | " |

As can be seen from the above data, very effective antibacterial properties can be provided to the polyurethane and the degree of the antibacterial properties can be controlled, as desired. This is an important feature of the invention, since the liberation of iodine in controlled amounts is of utmost importance in medical appliances, particularly appliances applied within the body. As can be easily appreciated, too little release of iodine will be ineffective, while too great a release of iodine would be quite undesirable.

EXAMPLE 2

A sparingly cross-linked polyurethane, (Estane-58300, manufactured by the B. F. Goodrich Co.) was tested and found to have an elongation of approximately 300% and Shore A hardness of 90. The polymer was placed in a conventional, single screw, heated barrel extruder with the die temperature controlled at 390° F. The die plate had a conventional spider die for extruding a tubular shape and the extruded polyurethane polymer, at room temperature, was in the form of semi-rigid, but yet bendable or flexible tube. Sections of the tube so extruded were cut and immersed in the 2% iodine solution of Example 1. After a dwell period of 1 hour, the tubes were washed with the same solvent as that of Example 1 and dried. The uptake of iodine produced a brown color in the tube and the intensity of that brown color is directly proportional to the iodine content in the tube.

The tube was placed at room temperature in a covered container, but opened to the atmosphere, whereby sublimation of the iodine could take place. After three months, the intensity of the brown color of the tube was compared to the intensity of the brown color of a freshly prepared tube, i.e. prepared in the identical manner. The intensity of the brown color of the test tube was only slightly less than the intensity of the brown color of the freshly prepared tube, demonstrating that no significant amount of the iodine had sublimated during the test.

Accordingly, it will be seen from the above that the objects of the invention have been achieved. It will also be appreciated that modifications of the invention, as specifically described above, will be apparent to those skilled in the art. Thus, it is intended that those apparent modifications be embraced by the spirit and scope of the annexed claims.

What is claimed is:

1. A polymeric bacteriocidal shaped form for medical use comprising a thermoplastic, sparingly cross-linked polyurethane having —NH—(C=O)—O— urethane linkages and/or urea linkages —NH—(C=O)—NH— and iodine complexed therewith, said complexed linkages being formed within said polyurethane so that said iodine provides bacteriocidal properties to said polyurethane, said bacteriocidal properties being at least sufficient to inhibit growth of *S. Aureus* and *Proteus Vulgaris* type bacteria, said polyurethane having an average molecular weight between 35,000 and 50,000, an ultimate elongation of 200 to 800 percent and a Shore A scale hardness of 60 to 95, said polyurethane being molded into said shaped medical article and thereafter being treated with a solution of iodine to increase the amount of iodine complexed at the linkage sites.

2. The shaped form of claim 1 wherein the number of complexed linkages is sufficient to render the composition self-sterilizing.

3. The shaped form of claim 1 wherein the shaped form is a medical or hospital appliance.

4. The shaped form of claim 1 wherein the shaped form is packaging film or a package.

5. The appliance of claim 3 in the form of a suture, catheter, tape, tubing, sponge, glove, surgical pad, cover or instrument.

6. The shaped form of claims 3 or 4 or 5 wherein the shaped form has iodine complexed with the said linkages on or near at least a part of the surface of the shaped form.

7. The shaped form of claim 1 wherein the complexed iodine is releasably complexed with said linkages and is slowly diffusible therefrom.

8. The method of producing the shaped form of claim 1, comprising shaping the said polyurethane and contacting the preformed shape with a solution of iodine.

9. The method of claim 8 wherein the shaped form is extruded, molded or cast.

10. The method of claim 8 where the solution is a tincture and/or aqueous solution.

11. The method of claim 8 wherein the concentration of iodine in the solution is at least 1% and up to 15%.

12. The method of claim 8 wherein the said contacting is at temperatures of from the freezing point of the solution up to the boiling point of the solution.

13. The method of claim 12 wherein the said temperature is between 20° C. and 60° C.

14. The method of claim 8 wherein the said contacting is continued for a period of at least 5 minutes.

15. The method of claim 14 wherein the said period is from 1 hour to 48 hours.

16. The method of claim 8 wherein after said contacting the shaped form is washed.

17. The method of claim 16 wherein the washing is with the solvent used to prepare the said iodine solution.

18. The method of claim 8 wherein the contacting is at elevated pressures.